US007455689B2

(12) United States Patent
Johnson

(10) Patent No.: US 7,455,689 B2
(45) Date of Patent: Nov. 25, 2008

(54) FOUR-LEAFLET STENTED MITRAL HEART VALVE

(75) Inventor: Derrick Johnson, Orange, CA (US)

(73) Assignee: Edwards lifesciences Corporation, Irvine, CA (US)

(*) Notice: Subject to any disclaimer, the term of this patent is extended or adjusted under 35 U.S.C. 154(b) by 287 days.

(21) Appl. No.: 11/212,373

(22) Filed: Aug. 25, 2005

(65) Prior Publication Data
US 2007/0050021 A1 Mar. 1, 2007

(51) Int. Cl.
A61F 2/24 (2006.01)
(52) U.S. Cl. .................................... 623/2.18; 623/2.14
(58) Field of Classification Search ........ 623/2.12–2.19
See application file for complete search history.

(56) References Cited

U.S. PATENT DOCUMENTS

| 4,366,581 | A | * | 1/1983 | Shah .......................... 623/2.41 |
| 5,326,372 | A | | 7/1994 | Mhatre et al. |
| 5,415,667 | A | | 5/1995 | Frater |
| 6,358,277 | B1 | | 3/2002 | Duran |
| 6,562,069 | B2 | | 5/2003 | Cai et al. |
| 6,767,362 | B2 | * | 7/2004 | Schreck ...................... 623/2.11 |
| 6,830,586 | B2 | | 12/2004 | Quijano et al. |
| 6,881,224 | B2 | | 4/2005 | Kruse |
| 6,936,067 | B2 | | 8/2005 | Buchanan |
| 2002/0091441 | A1 | | 7/2002 | Guzik |
| 2003/0069635 | A1 | * | 4/2003 | Cartledge et al. .......... 623/2.13 |
| 2003/0118560 | A1 | | 6/2003 | Kelly et al. |
| 2003/0229394 | A1 | | 12/2003 | Ogle et al. |
| 2004/0024452 | A1 | | 2/2004 | Kruse et al. |
| 2004/0186558 | A1 | | 9/2004 | Pavenik et al. |
| 2005/0096738 | A1 | | 5/2005 | Cali et al. |
| 2005/0137682 | A1 | | 6/2005 | Justino |

OTHER PUBLICATIONS

Hofmann, et al., Early eperience with a quadrileaflet stentless mitral valve, 71 (5 Supp) pp. 323-326 Annals of Thoracic Surgery, 2001.

* cited by examiner

Primary Examiner—Thomas J Sweet
Assistant Examiner—Jonathan R Stroud
(74) Attorney, Agent, or Firm—Rajiv Yadav; Guy Cumberbatch

(57) ABSTRACT

A prosthetic mitral heart valve having four separate flexible leaflets. The heart valve includes a support frame that may be non-circular, for example elliptical or "D-shaped". The support frame may have an undulating outflow edge defined by four inflow cusps and four outflow commissures to which each of the flexible leaflets attaches. The support frame may comprise an undulating wireform and a surrounding stent defining a structure having four cantilevered posts projecting in the outflow direction to support the four leaflets. The heart valve is designed to be secured in the annulus and function as a standalone unit without papillary muscle connections to the leaflets. The four leaflets may be arranged in two opposed pairs, one pair being smaller than the other pair. The larger pair of leaflets may be identical, or differently sized. Existing sizes of heart valve leaflets may be utilized with the smaller leaflets being at least two leaflet sizes smaller than the larger leaflets in odd millimeter increments.

19 Claims, 5 Drawing Sheets

FOUR-LEAFLET STENTED MITRAL HEART VALVE

FIELD OF THE INVENTION

The present invention relates generally to an implantable prosthetic heart valve for the mitral annulus and, more particularly, to a four-leaflet prosthetic heart valve having a non-circular flow orifice.

BACKGROUND OF THE INVENTION

The most common locations at which prosthetic heart valves are implanted are the aortic and mitral valves associated with the left ventricle, which generates the higher pressures of the two ventricles. The anatomy of the aortic and mitral valves are quite different, with the former being a tri-symmetric/tri-leaflet structure, and the latter having two dissimilar leaflets. The aortic annulus defines an undulating fibrous structure around substantially a circular ring to support the up-and-down shape of the cusps and commissures of the native leaflets. On the other hand, the mitral annulus has a somewhat fibrous linear anterior aspect across the septum of the heart from the aortic valve, but the posterior aspect, which defines the majority of the annulus, is relatively less fibrous and more muscular. Also, the posterior aspect is nearly oval-shaped such that the mitral annulus presents a malformed "D" shape. The present invention is directed to prosthetic heart valves particularly suited for implant at the mitral annulus.

The left ventricle LV and valves associated therewith are depicted in FIG. 1 as seen in vertical cross-section along an anterior-posterior plane. The mitral valve MV controls flow from the left atrium LA to the left ventricle LV, while the aortic valve AV functions between the left ventricle LV and ascending aorta AA. Both the mitral valve and aortic valve include leaflets that extend into the blood flow path and are supported around their peripheries by respective fibrous annuluses. For purpose of discussion, the mitral annulus of a normal, healthy heart lies generally in a mitral annulus plane MAP defined perpendicular to the average blood flow direction 20 (see FIG. 1) through the mitral valve MV. Although a typical mitral annulus may be three-dimensional, the mitral annulus plane MAP will be used as a reference plane that extends through the posterior aspect of the annulus. Papillary muscles are not shown but attach to the lower portion of the interior wall of the left ventricle LV and chordae tendineae extend between and link the papillary muscles and free edges of the anterior and posterior leaflets.

FIG. 2 illustrates in plan view the mitral valve MV from the left atrium as exposed during surgery, while FIG. 2A schematically identifies the commonly identified features. The anterior aspect of the mitral annulus forms a part of the "cardiac skeleton" and includes anteriolateral ALT and posteriomedial PMT fibrous trigones. The mitral valve MV is a bicuspid valve having a posterior leaflet (separated into three cusps $P_1$, $P_2$, $P_3$) that cooperates or coapts with an anterior leaflet A. The anteriolateral ALT and posteriomedial PMT trigones are indicated at the junctions between the anterior leaflet A, and the first and third cusps of the posterior leaflet $P_1$, $P_3$, respectively. The trigones are also sometimes known as commissures.

As mentioned above, and with reference to FIG. 2A, the mitral annulus has a malformed "D" shape in plan view with the straight portion, or anterior aspect, extending between the anteriolateral ALT and posteriomedial PMT trigones. The longest dimension of the mitral annulus defines a major axis 22 while the shortest dimension defines a perpendicular minor axis 24. The minor axis 24 generally bisects the anterior leaflet A. Although the mitral annulus is not circular, a center 26 thereof can be defined at the intersection of the major and minor axes 22, 24. Radial lines can be drawn outward from this imaginary center 26 through the anteriolateral ALT and posteriomedial PMT trigones to indicate the angular separation φ therebetween. This angular separation φ varies from patient to patient, but is generally about one-third of the circumference around the mitral annulus, or between 120°-125°.

Two primary types of heart valve replacements or prostheses are known: rigid leaflet or ball-type mechanical valves, and "bioprosthetic" valves having flexible leaflets supported by a peripheral frame. The flexible leaflets of bioprosthetic valves project into the flow stream and function much like those of a natural human heart valve, imitating their natural flexing action to coapt against each other and ensure one-way blood flow. In tissue-type valves, a whole xenograft valve (e.g., porcine) or a plurality of xenograft leaflets (e.g., bovine pericardium) typically provide fluid occluding surfaces. Synthetic leaflets have been proposed, and thus the term "flexible leaflet valve" refers to both natural and artificial "tissue-type" valves. One example of a flexible leaflet valve is disclosed in U.S. Pat. No. 5,928,281 to Huynh, et al. (Edwards Lifesciences, Corp., Irvine, Calif.), the disclosure of which is hereby expressly incorporated by reference.

Bioprosthetic valves may be "stented, " wherein two or more flexible leaflets are mounted within a metallic or polymeric peripheral support frame that usually includes posts or commissures extending in the outflow direction to mimic natural fibrous commissures in the native annulus. The support frame includes an undulating outflow edge including alternating inflow cusps and outflow commissures. The commissures are often flexible and extend generally axially in the outflow direction in a cantilevered fashion so as to be fixed at the inflow end and be capable of flexing along their lengths and distributing the forces associated with blood flow. One commonly used peripheral support frame is a flexible, undulating wire, sometimes called a "wireform, " which has a plurality (typically three) of large radius cusps supporting the cusp region of the flexible leaflets (i.e., either a whole xenograft valve or three separate leaflets). The ends of each pair of adjacent cusps converge somewhat asymptotically to form upstanding commissures that terminate in tips, each extending in the opposite direction as the arcuate cusps and having a relatively smaller radius. This provides an undulating reference shape to which a fixed edge of each leaflet attaches (via components such as fabric and sutures) much like the natural fibrous skeleton in the aortic annulus. One example of the construction of a flexible leaflet valve is seen in U.S. Pat. No. 5,928,281. Other "support frame" constructions exhibit sheet-like tubular shapes but still define undulating commissures and cusps on their outflow ends, such as shown in U.S. Pat. No. 5,984,973 to Gerard, et al. Components of the valve are typically assembled with one or more biocompatible fabric (e.g., Dacron) coverings, and a fabric-covered sewing ring is provided on the inflow end of the support frame.

Many other stented flexible leaflet valve configurations are known, including U.S. Pat. No. 6,086,612 to Jansen (Adiam Medizintechnik GmbH & Co. KG, Germany) which discloses a mitral valve prosthesis having a support housing with a large base ring (12) that bears two stays (18, 19) which substantially extend in the ring axis direction and are connected by curved walls for securing two flexible synthetic cusps (leaflets). The free ends of the stays form an inner support for the cusps. The base-ring has in the top view a closed, non-round shape with a common longitudinal axis (15) but two transverse half-axes (16, 17) of different sizes.

"Stentless" prosthetic valves have essentially no rigid elements coupled to the flexible leaflets and an annular support frame so as to limit movement constraints. An example of a stentless valve is seen in U.S. Pat. No. 5,415,667 to Frater. Frater discloses a four-leaflet mitral heart valve replacement of essentially flexible bioincorporable material. The valve includes a generally D-shaped (30) sewing ring having an opening (31) with a long straight side (32), a shorter side (35) opposite the longer side, and lateral sides of the opening (31) extending between adjacent ends of the long and short sides. An anterior cusp (33) hinges on the long side, a posterior cusp (34) hinges on the shorter side portion (35), and two lateral cusps (36A & 36B) hinges on each of the remaining sides. Chordae of bioincorporable material extend from edges of the cusps for connection to the papillary muscles in the cavity of the ventricle when the sewing ring is sutured to the atrioventricular junction of the patient's heart.

The Frater four-leaflet mitral valve design has been clinically investigated as the quadrileaflet mitral valve (SJM-Quattro-MV). The SJM-Quattro-MV is a stentless bioprosthesis made of bovine pericardium with standard glutaraldehyde tanning and additional anticalcification treatment with polyol. The valve consists of a large anterior and posterior leaflet and two small commissural cusps. The leaflets have straight hinge lines to avoid the excessive flexion stress of stented prostheses. The annulus is made of a three-layer pericardium and serves as a flexible annuloplasty device as well. Chordal support consists of two papillary flaps that support the anterior and posterior cusps.

Numerous prosthetic mitral heart valves have been proposed in the art, typically without too much consideration of the unique attributes of the mitral annulus. In particular, they have been no commercially successful attempts to modify conventional prosthetic valves to better conform to the mitral annulus.

SUMMARY OF THE INVENTION

The present invention provides a prosthetic heart valve for implant at a valve annulus, comprising a support frame defining a non-circular orifice about an axis along an inflow-outflow direction. Four separate flexible leaflets each separately mounted for movement on the support frame to provide a one-way valve in the elliptical orifice. In one embodiment, the support frame defines an elliptical orifice, and the four leaflets may be arranged into pairs of diametrically opposed, symmetric leaflets. In a particular embodiment, each one of the first pair of leaflets is substantially smaller than either leaflet of the second pair. Alternatively, the support frame may define a D-shaped orifice wherein the leaflets on the second pair are differently sized. Desirably, the support frame comprises an undulating outflow edge including four alternating inflow cusps and flexible outflow commissures that extend generally axially in the outflow direction in a cantilevered fashion. Each of the separate flexible leaflets has a cusp edge mounted to an inflow cusp of the support frame and two commissure edges mounted to adjacent outflow commissures of the support frame.

In another aspect of the invention, a prosthetic heart valve for implant at a valve annulus is provided. The heart valve includes a support frame defining an orifice about an axis along an inflow-outflow direction, the support frame having an undulating outflow edge including four alternating inflow cusps and flexible outflow commissures that extend generally axially in the outflow direction in a cantilevered fashion. Four separate flexible leaflets each separately mount for movement along the outflow edge of the support frame to provide a one-way valve in the orifice. Each leaflet includes a cusp edge mounted to an inflow cusp of the support frame and two commissure edges mounted to adjacent outflow commissures of the support frame. The support frame may define an elliptical orifice, the valve may be symmetric about two axes, or the support frame may define a D-shaped orifice. Desirably, the support frame comprises an undulating wireform and a stent therearound, the wireform generally defining the outflow edge of the support frame and having inverted V-shaped commissures through which the commissure edges of two adjacent leaflets extend. The stent has commissure posts of approximately the same height as the wireform commissures to which the extending commissure edges attach. The wireform and stent are preferably made of synthetic materials, while a leaflets are made of a biological sheet material such as bovine pericardium. Preferably, the support frame commissures have an axial height of at least 6 mm.

In a still further aspect, a prosthetic heart valve for implant at a valve annulus is provided that comprises a support frame defining an orifice about an axis along an inflow-outflow direction. Four separate flexible leaflets each separately mount for movement on the support frame to provide a one-way valve in the orifice, wherein at least one of the leaflets is substantially smaller than at least one of the other leaflets. In one embodiment, four leaflets comprise a first pair and a second diametrically opposed pair of leaflets, with each leaflet of the first pair being substantially smaller than either leaflet of second pair. For example, the two leaflets of the first pair may be identically size, and the two leaflets of the second pair may also be identically sized. Desirably, support frame defines a noncircular orifice that is elliptical or D-shaped.

A further understanding of the nature and advantages of the present invention are set forth in the following description and claims, particularly when considered in conjunction with the accompanying drawings in which like parts bear like reference numerals.

DESCRIPTION OF THE PREFERRED EMBODIMENTS

Figure 1:
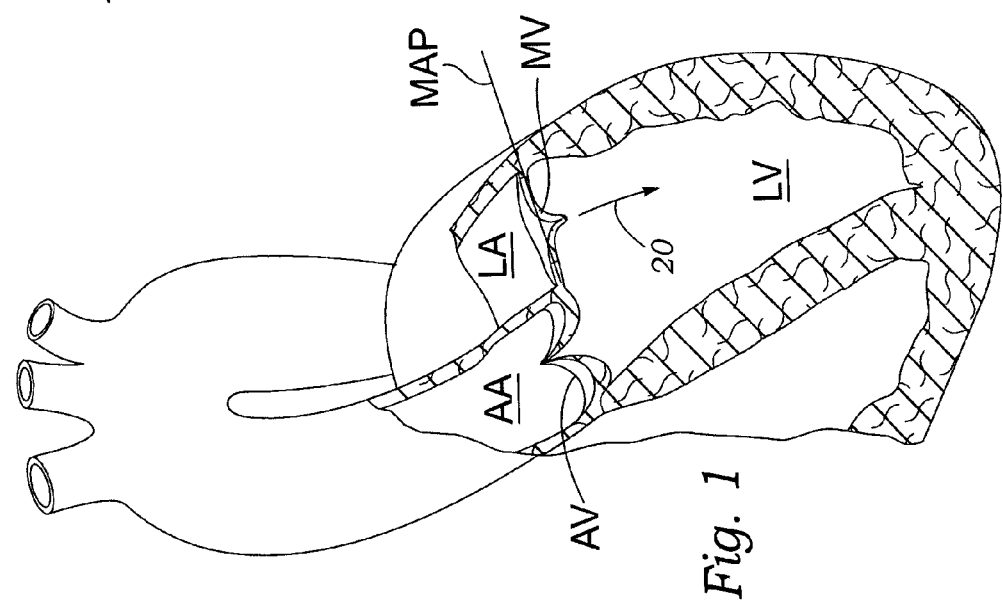
FIG. 1 is a view of the heart illustrating the left ventricle LV and valves associated therewith as seen in partial vertical section along an anterior-posterior plane.

The present invention pertains to prosthetic heart valves that simulate the natural human heart valve anatomy, in particular for the mitral valve. For instance, the shape of the flow orifice may be non-circular so as to mimic the shape of the mitral annulus in the systolic phase, or there may be four leaflets with one or more substantially smaller than the others. In a preferred embodiment, four leaflets are utilized with two opposed pairs that are substantially different from each other. More specifically, an exemplary heart valve of the present invention includes a first pair and a second pair of leaflets, each pair diametrically opposed across the valve orifice, and wherein each leaflet of the first pair is substantially smaller than either leaflet of the second pair.

The reader will see from the following description and appended drawings various features of the exemplary valves that are intended to mimic the natural mitral valve. It should be noted, however, that one or more of these features may be applicable to prosthetic valves for implantation in other than the mitral position, such as in the pulmonary position. As such, unless a feature is specifically applicable to the mitral position the invention should not be considered so limited.

Several considerations drive the development of the exemplary heart valve disclosed herein. For instance, in the mitral position the native anatomy comprises a relatively large anterior leaflet extending between the fibrous trigones and a posterior leaflet commonly subdivided into three scalloped cusps. In the systolic phase, the mitral annulus generally assumes an oval or elliptical shape with a short or minor axis approximately bisecting the anterior leaflet, midway between the fibrous trigones. Conventional prosthetic heart valves have circular support frames creating a circular orifice, which may not be an optimum shape to facilitate active opening of the leaflets and maximum flow through the orifice. A circular orifice implanted in the non-circular mitral annulus may create areas of static or stagnant blood flow because of the mismatched shapes. Further, the stress distribution on a circular heart valve may be undesirable, leading to decreased longevity. Finally, the implantation of a circular valve within a non-circular annulus may initiate tissue ingrowth in certain areas around the periphery of the valve.

The present invention provides a valve with a support frame defining an orifice that mimics the shape of the mitral annulus in the systolic phase and facilitates active opening of the leaflets and better blood flow. In addition, the more naturally-shaped orifice in conjunction with leaflets that better simulate the native leaflets is believed to reduce stresses imposed on various components of the prosthetic valve because the structure more faithfully simulates the native anatomy. Less stress on the valve may lead to a more durable implant.

One of the features that makes the present prosthetic heart valve more anatomically approximate is the provision of four (4) flexible leaflets. For definitional purposes, heart valves of the present invention are of the flexible leaflet type, as opposed to mechanical valves with rigid leaflets or balls for occluding members. The term "flexible leaflet" encompasses bioprosthetic (i.e., biological) leaflets such as bovine pericardium or leaflets in whole xenograft (e.g., porcine) valves, bioengineered leaflets, and synthetic leaflets. The flexible leaflets are mounted from a peripheral support frame so as to project inward into a flow orifice defined thereby.

The term "support frame" broadly covers non-biological structures having wireforms, stents, and the like. For example, the exemplary embodiment of the present invention includes an undulating cloth-covered wireform to which peripheral edges of three leaflets are sewn. The term "cloth" as used herein encompasses a variety of biocompatible fabrics, the most commonly used being polyester terepthalate. Additionally, a dual-band stent surrounds the wireform and provides additional support for the leaflets. Another possible support frame is disclosed in U.S. Pat. No. 6,350,282 assigned to Medtronic, Inc. of Minneapolis, Minn. A still further support frame disclosed in U.S. Pat. No. 5,824,069 assigned to Medtronic, Inc. has a "stent" that supports flexible leaflets. The stent defines an undulating outflow edge, similar to a wireform. It should also be noted that a "wireform" could be made from a variety of materials, including biocompatible metals such as Elgiloy and polymers such as Delrin. Another "support frame" that can be modified to incorporate certain features of the present invention is shown in U.S. Pat. No. 6,610,088 to Gabbay and includes a "stent" with an undulating outflow edge that provides support for flexible leaflets.

Finally, the term "support frame" encompasses conventional heart valve stents/wireforms designed to be delivered during open heart surgery, and also compressible/expandable support frames designed for minimally-invasive surgeries, such as shown in U.S. Pat. No. 5,411,552 to Andersen, et al. The patent to Anderson, et al. also discloses a whole cardiac valve connected to the stent structure which, as mentioned, is a variation also covered by the term "flexible leaflets."

Figure 3B:
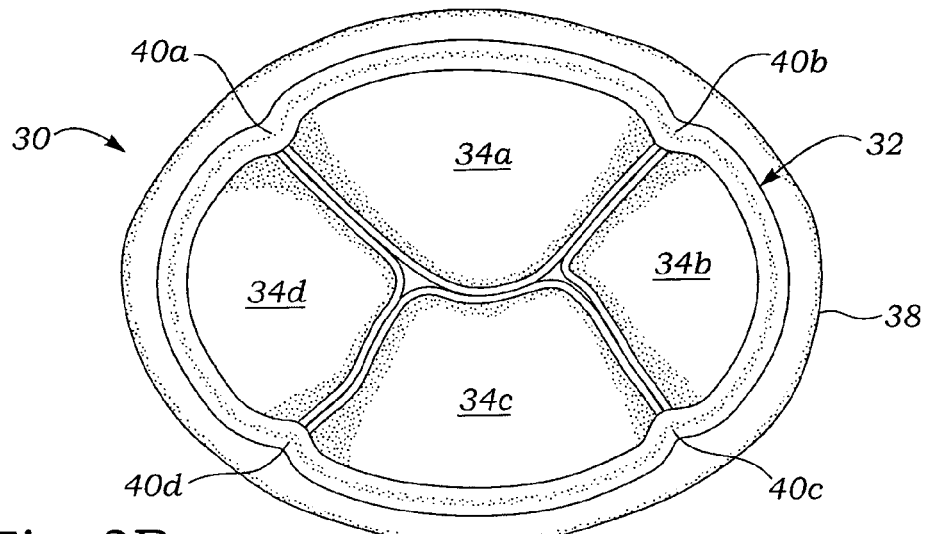
FIGS. 3B-3C are outflow plan and side elevational views, respectively, of the four-leaflet prosthetic heart valve of FIG. 3A.
Figure 3A:
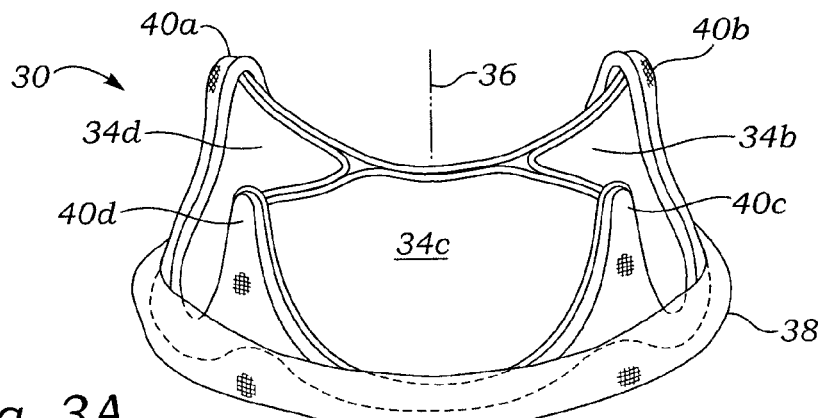
FIG. 3A is a perspective view of an exemplary four-leaflet prosthetic heart valve of the present invention.
Figure 3C:
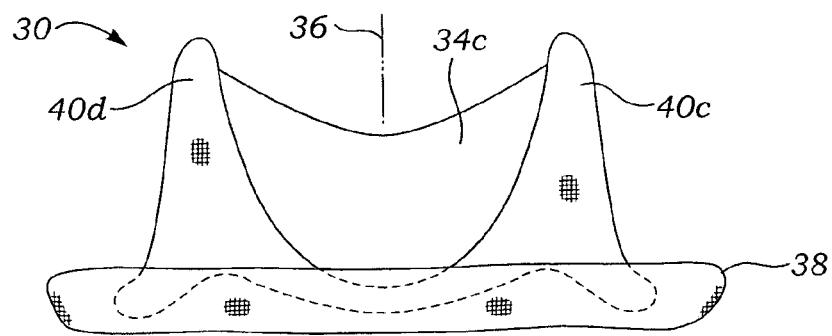

With reference now to FIGS. 3A-3C, an exemplary prosthetic heart valve 30 of the present invention is shown in various views. The heart valve 30 includes a peripheral support frame 32 from which four flexible leaflets 34*a*, 34*b*, 34*c*, 34*d* project inwardly toward a central flow axis 36. The flow axis 36 extends along an inflow-outflow direction, with the outflow end of the valve 30 being directed upwards in FIG. 3A. A suture or sewing ring 38 attaches around the outside of the support frame 32 and provides a platform through which attachment structure may be passed to hold the valve 30 in place within the body. Typically, heart valves are secured within the affected annulus using an array of sutures passed through the sewing ring 38, although staples, clips, and other such devices may alternatively be used. The sewing ring 38 is shown lying generally within a plane that is perpendicular to the flow axis 36. However, a contoured sewing ring 38 may also be utilized, such as disclosed in co-pending U.S. Patent Publication No. 2007-0016289, filed Jul. 13, 2005, and entitled "PROSTHETIC MITRAL HEART VALVE HAVING A CONTOURED SEWING RING," the disclosure of which is hereby expressly incorporated by reference.

The heart valve 30 includes four commissures 40*a*, 40*b*, 40*c*, 40*d* that project in the outflow direction. The upper tips of the commissures 40*a*, 40*b*, 40*c*, 40*d*, define an outflow end of the valve 30 while the lower extremity of the sewing ring 38 defines an inflow end. As with many conventional flexible leaflet valves, the four leaflets 34*a*, 34*b*, 34*c*, 34*d* project into the flow orifice toward the axis 36 and curl against one another in the outflow direction to "coapt" and occlude blood flow in one direction. The valve 30 is shown in the figures in its closed state with the four leaflets 34*a*, 34*b*, 34*c*, 34*d* coapting together along lines radiating generally from the flow axis 36 (see FIG. 3B). The commissures 40*a*, 40*b*, 40*c*, 40*d* are flexible and extend in a cantilevered fashion, fixed at their inflow ends and capable of flexing along their lengths and distributing the forces associated with blood flow.

The support frame 32 defines a non-circular flow orifice within which the four leaflets are supported. In the exemplary configuration of FIG. 3B, the horizontal dimension of the support frame 32 is greater than the vertical dimension, creating somewhat of an elliptical or oval shape. When utilized in the mitral position, the peripheral shape of the support frame 32 is desirably in the shape of the mitral annulus in its systolic phase, which is substantially elliptical or D-shaped.

Figure 2:
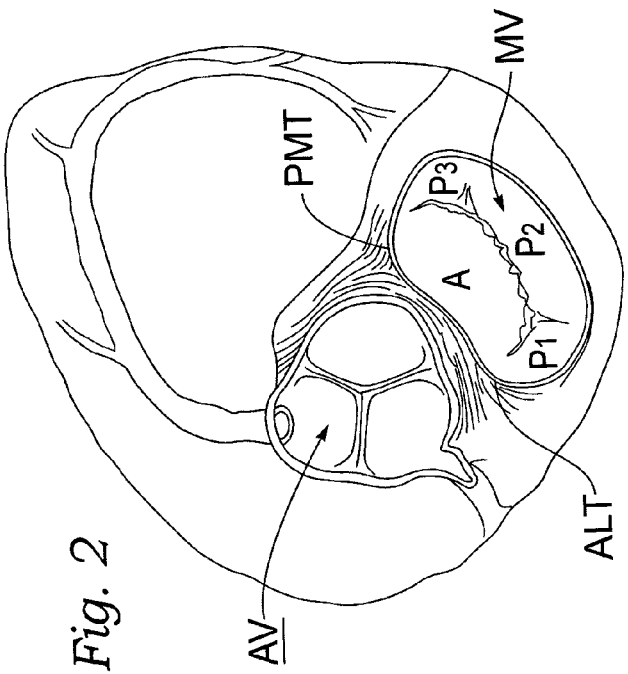
FIG. 2 is a view from above of the aortic and mitral annuluses exposed by removal of the respective atria.
Figure 2A:
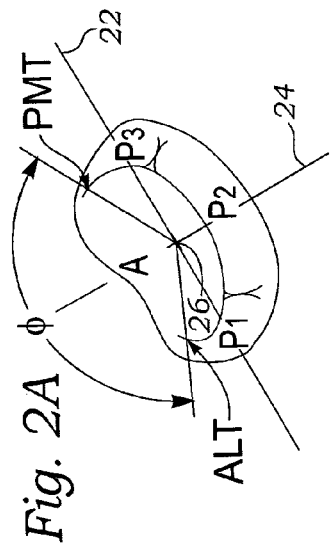
FIG. 2A is a schematic view of the mitral annulus corresponding to be viewed in FIG. 2 and indicating the most prominent anatomical features and nomenclature.

Still with reference to FIGS. 3A-3C, when the heart valve 30 is to be used in the mitral position, the leaflets 34a, 34b, 34c, 34d are oriented to approximately mirror the native leaflet orientation and relative sizes. That is, that the first leaflet 34a extends between first and second commissures 40a, 40b that are spaced apart around the circumference of the valve 30 at the approximate location of the fibrous trigones of the mitral annulus (see FIG. 2A). Therefore, the first leaflet 34a simulates the anterior leaflet of the mitral valve, and the upper portion of the valve 30 as shown in FIG. 3B between the commissures 40a, 40b represents an anterior aspect thereof. The remainder of the periphery of the valve 30 (extending the long way around the valve periphery between the commissures 40a, 40b) represents a posterior aspect, and the three leaflets 34b, 34c, 34d together simulate the posterior leaflet. Of course, the valve 30 must be implanted in this orientation to obtain the intended benefits. Alternatively, of course, if the valve 30 is symmetric about its long axis such that the leaflets 34a and 34c are identical, then the valve 30 may be rotated 180° and function in the same manner.

Prior to a further description of the various alternatives of the four-leaflet prosthetic heart valve of the present invention, an exemplary internal support frame construction will be presented. As mentioned above, a support frame for the flexible leaflets may be formed from a variety of elements. The present application discloses a wireform and surrounding stent that are both cloth-covered and work together to support the leaflets therein. Specifically, FIGS. 4A-4C illustrate an exemplary wireform 50, while FIGS. 5-9 illustrate an exemplary stent 52.

Figure 4B:
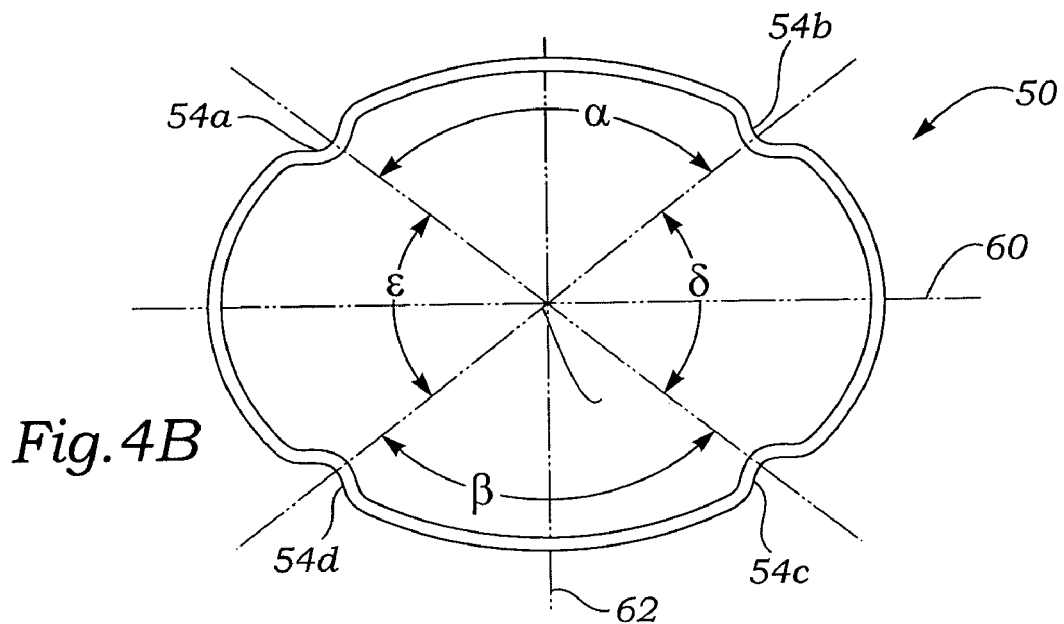
FIGS. 4B-4C are outflow plan and side elevational views, respectively, of the wireform of FIG. 4A.
Figure 4A:
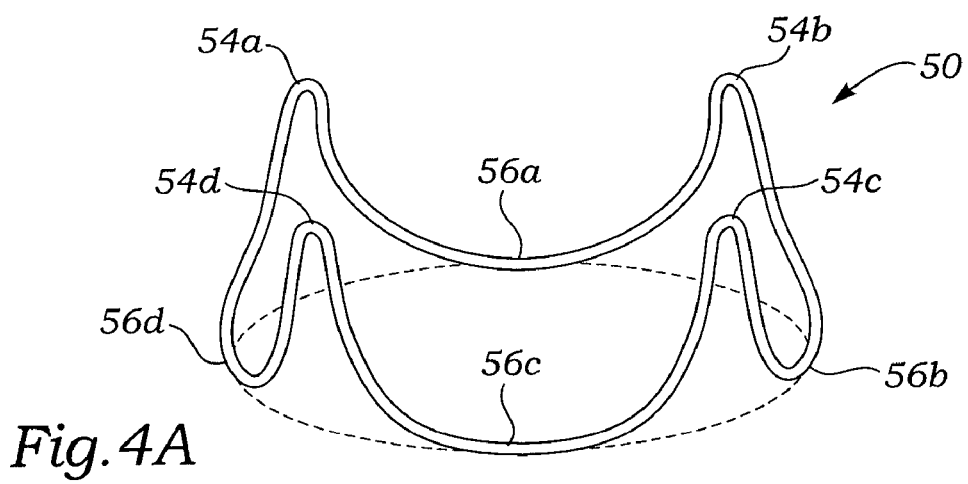
FIG. 4A is a perspective view of an exemplary wireform for the four-leaflet prosthetic heart valve of FIG. 3A.
Figure 4C:
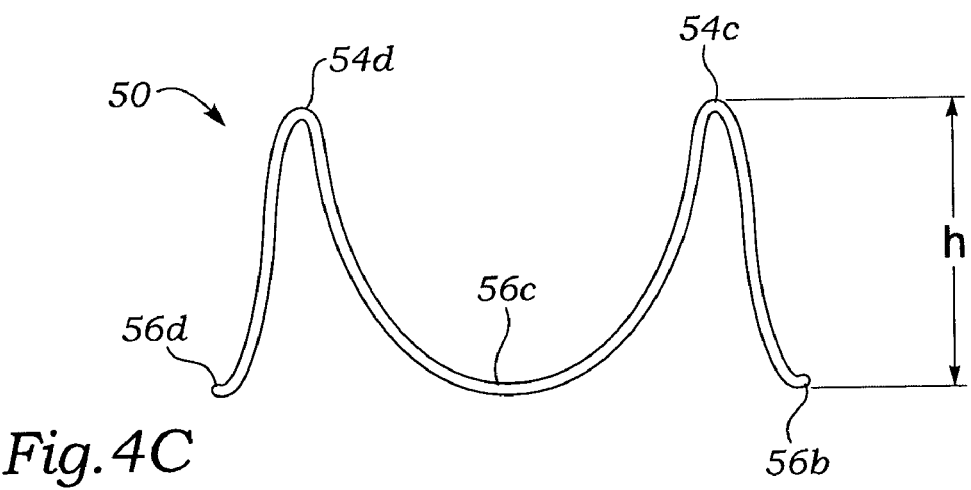

With reference to FIGS. 4A-4C, the exemplary wireform 50 comprises an elongated, undulating wire- or rod-like structure that defines four upstanding commissures 54a, 54b, 54c, 54d alternating with four arcuate cusps 56a, 56b, 56c, 56d. The ends of each pair of adjacent arcuate cusps 56 converge somewhat asymptotically to form the upstanding commissures that terminate in inverted V-shaped tips. The plan view of FIG. 4B shows a generally elliptical shape of the wireform 50 arranged about a major axis 60 and a minor axis 62 that are perpendicular to one another and intersect along the flow axis 36. As an approximate rule of thumb, the ratio of the minor axis (vertical) dimension to the major axis (horizontal) dimension is approximately 3:4, although it is believed that a ratio of 4:5 may be equally suitable for the exemplary prosthetic mitral valve 30. The commissures 54 tilt slightly radially inwardly from the cusps 56 such that their tips are closer together, as seen in FIG. 4B, and the wireform 50 generally defines a conical surface of revolution. The total height h of the wireform 50 is seen in FIG. 4c, and is preferably at least 6 mm, and more preferably between about 8 and 20 mm. Because of the non-circular shape of the valve orifice, and in particular with elongated orifices, the leaflets will be longer and also the commissure heights will be greater than with conventional circular valves.

As indicated in FIG. 4B, and measuring all angles in the clockwise direction, the angular distance α around the wireform 50 (and valve support frame 32) between the first and second commissures 54a, 54b, and the angular distance β between the third and fourth commissures 54c, 54d is substantially greater than the angular distance δ between the second and third commissure commissures 54b, 54c, or the angular distance ε between the fourth and first commissures 54d, 54a. When used as a mitral valve, the angular distance α represents an anterior aspect of the wireform 50 (or valve 30), while the combined angular distances β, δ, ε represents the posterior aspect of the valve 30. In a preferred embodiment, the angular distance α is between about 120°-125°.

Figure 5:
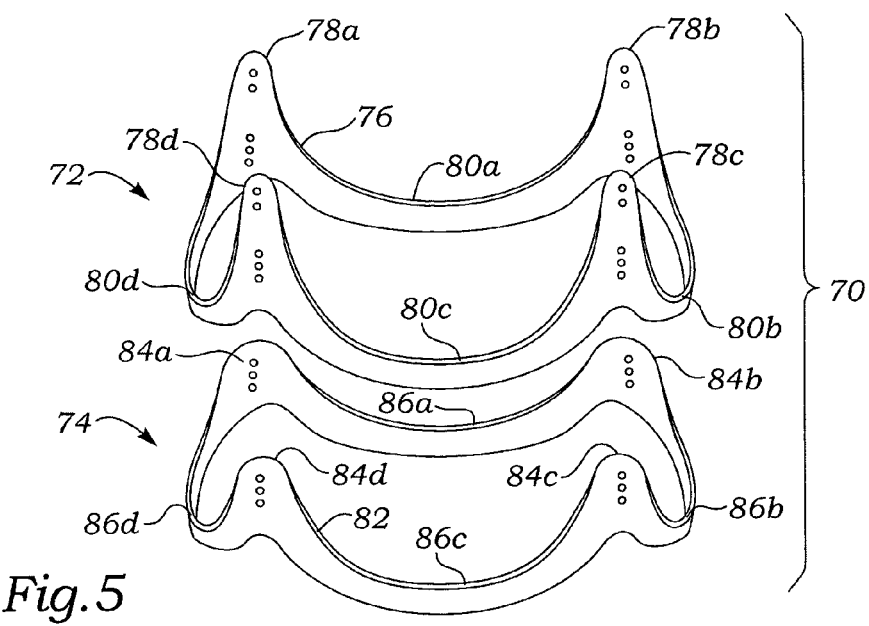
FIG. 5 is a perspective exploded view of an exemplary stent for use with the wireform of FIG. 4A in the four-leaflet prosthetic heart valve of FIG. 3A.
Figure 6:
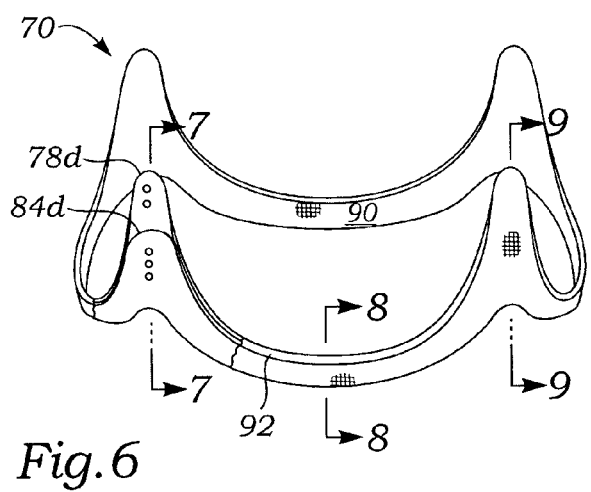
FIG. 6 is a perspective assembled view of the stent of FIG. 5 shown partially fabric-covered.

FIGS. 5 and 6 illustrate, respectively, exploded and assembled views of a stent 70 that forms a part of the valve support frame 32. The stent includes a primary band 72 and a secondary band 74 surrounding the primary band. The primary band 72 defines a closed shape and includes an outflow edge 76 similar to the wireform 50 described above with alternating commissure sections 78a, 78b, 78c, 78d and cusp sections 80a, 80b, 80c, 80d. The secondary band 74 also defines a closed shape similar to the primary band, and has an outflow edge 82 with commissure sections 84a, 84b, 84c, 84d and cusps sections 86a, 86b, 86c, 86d. The outflow edge 76 of the primary band 72 is shaped to closely follow the contours of the wireform 50. The commissure sections 84 of the secondary band outflow edge 82 are truncated with respect to those of the primary band 72.

Figures 7, 9:
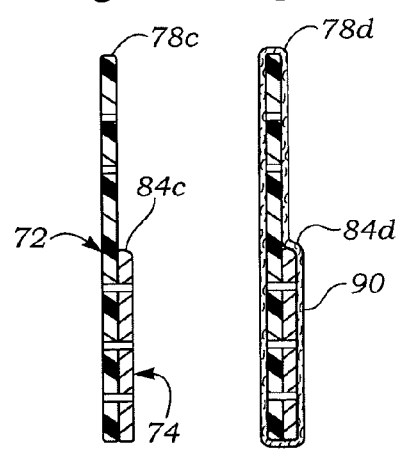
FIGS. 7-9 are sectional views through cusps and commissures of the stent taken along radial planes as indicated in FIG. 6.
Figure 8:
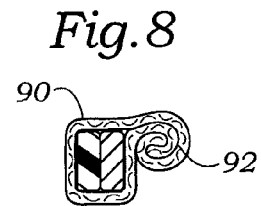

As seen by the assembled view of FIG. 6, and the cross-sections of FIGS. 7-9, the secondary band 74 closely surrounds and is coupled to the primary band 72. Although not numbered, the inflow edges of the two bands 72, 74 coincide to form a single common inflow edge in the assembled combination. FIG. 6 illustrates in partial cut-away a cloth covering 90 encompassing the combination. The cloth covering 90 is rolled into a cuff 92 that extends outward from the two bands along the cusp sections 80, 86, and partially up the commissure sections 78, 84. The cuff 92 is seen in cross-section in FIG. 8 and provides a sewing rim facilitating assembly of the valve, as will be described below. The two bands 72, 74 include a number of radial holes through which coupling sutures (not shown) can be passed for joining the two bands together, and for securing the cloth covering 90 to the combination.

In a preferred embodiment, the primary band 72 is formed of a material that is relatively more flexible than the secondary band 74. As will become clearer below, the flexible leaflets of the valve attach to the uppermost portions of the commissures of the flexible primary band 72, which does not inhibit flexing of the valve commissures during the systolic, or valve closing, phase. Conversely, the more rigid secondary band 74 provides stability to the basic structure around the inflow edge and cusps. For example, the primary band 72 may be formed of a polymer such as Delrin while the secondary band 74 is form of a metallic alloy such as Elgiloy.

In one exemplary embodiment of the invention, a collection of differently-sized prosthetic heart valve leaflets may be used to construct the four-leaflet mitral heart valve 30. Conventional, circular heart valves are labeled by the diameter of their orifice, typically between 25 millimeters and 33 mm in odd increments (i.e., 25-27-29-31-33), which provides an adequate selection of sizes for most patients. For definitional purposes, a 29 mm heart valve 30 of the present invention has a trigone-trigone dimension of 29 mm. An exemplary heart valve 30 of the present invention may utilize two larger leaflets 34a, 34c and two smaller leaflets 34b, 34d. The non-circular shape of the valve orifice likely necessitates a leaflet shape different from those found in conventional circular-orifice valves. For instance, the larger leaflets 34a, 34c are proportionally longer across their free edges relative to their height than the smaller leaflets 34b, 34d, and also relative to conventional leaflets.

The larger pair of first and third leaflets 34a, 34c may be slightly thicker than the smaller pair of second and fourth leaflets 34b, 34d. Because of the larger area of the first and third leaflets 34a, 34c, they will be subjected to a greater overall force from the pressure of the blood flow when the valve closes (the systolic phase of the mitral valve). Therefore, at least for bioprosthetic tissue such as bovine pericardium, it is desirable that the larger leaflets 34a, 34c be made somewhat more robust than the other two leaflets to have a comparable usable life (i.e., durability). In one embodiment, the thickness of the larger leaflets 34a, 34c is between about 10-100% greater than the thickness of the smaller two leaflets.

In accordance with an exemplary fabrication method, the leaflet selection methodology disclosed in U.S. Pat. No. 6,245,105 (expressly incorporated herein) may be used to provide stronger tissue for the larger leaflets 34a, 34c than for the other leaflets. The selection methodology utilizes one or more tests, for example a deflection test, to determine the relative elasticity or stiffness of each leaflet. Because of the non-uniform nature of certain bioprosthetic tissue, for example bovine pericardium, the same size leaflets cut from different portions of tissue may have different mechanical properties. In accordance with an exemplary fabrication method, relatively stronger (e.g., stiffer) leaflets are selected for use as the larger leaflets 34a, 34c, but relatively softer membrane-like leaflets are used as the smaller leaflets 34b, 34d. It should be noted that these characteristics can generally be predicted merely from measuring the thickness of the tissue, but the supplemental selection methodology disclosed in U.S. Pat. No. 6,245,105 is desirably used to further distinguish between leaflets of the same thickness.

Figure 10:
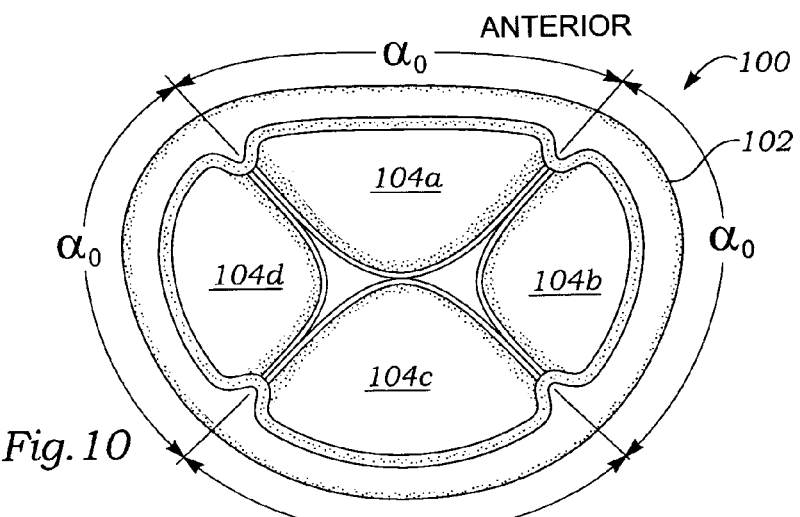
FIGS. 10-12 are outflow plan views of alternative four-leaflet prosthetic heart valves having dissimilar leaflets.
Figure 11:
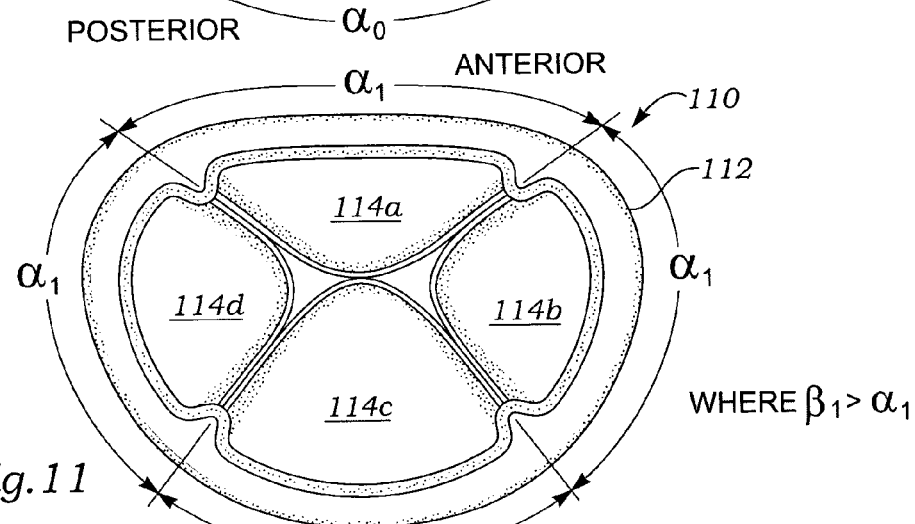
Figure 12:
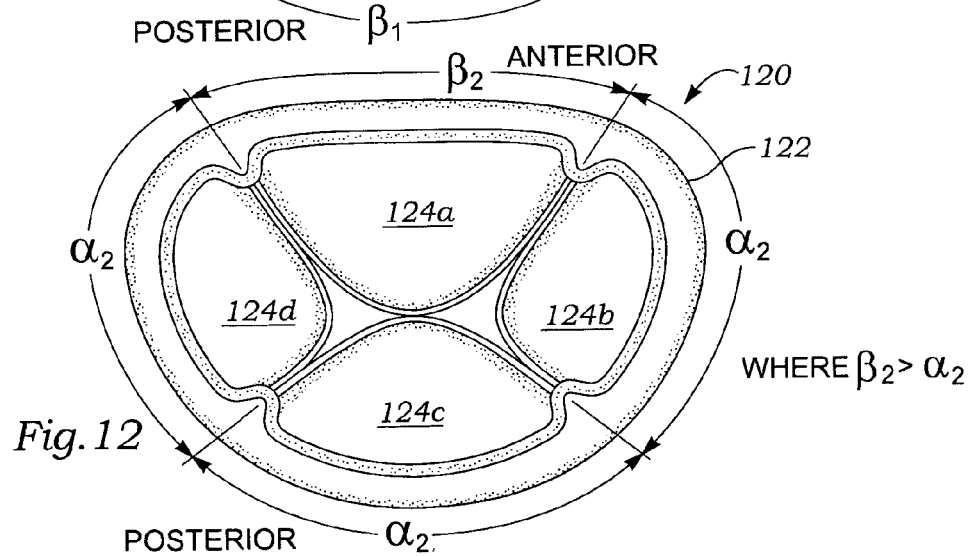

FIGS. 10-12 are outflow plan views of alternative four-leaflet prosthetic heart valves 100, 110, 120 of the present invention having dissimilar leaflets. Each of these valves has a peripheral support frame 102, 112, 122, that defines a flow orifice that is non-circular in plan view to match the mitral annulus. More specifically, the flow orifices have a rounded D-shape with a somewhat straighter side at the top opposite a more rounded side at the bottom. The left and right sides are somewhat shorter than the top and bottom sides to result in a modified elliptical shape. The more straighter top side conforms to the anterior aspect of the mitral annulus, while the remainder of the flow orifice conforms to the posterior aspect. As was explained above with respect to FIGS. 1-2A, the mitral annulus is a bi-leaflet valve with an anterior leaflet between the fibrous trigones and a posterior leaflet around the rest of the annulus. The posterior leaflet is, however, characterized by three cusps.

In FIG. 10, the prosthetic heart valve 100 includes four substantially identical leaflets 104a, 104b, 104c, 104d around the periphery. Lines radiating outward from the flow axis (not numbered) extend through the commissures of the valve 100. The identical angular size of each of the leaflets is indicated by the angle $\alpha_0$ within each quadrant, which angle $\alpha_0$ is approximately 90°. Because of the asymmetric shape of the flow orifice in plan view, each of the leaflets 104a, 104b, 104c, 104d may be differently configured even though they span the same angular dimension. Alternatively, each of the leaflets may be identically configured with the understanding that the slack that they each possess will permit them to coapt with each other within the flow orifice. In this valve 100, the upper leaflet 104a substantially corresponds to the native anterior leaflet, while the remaining three leaflets 104b, 104c, 104d combine to simulate the native posterior leaflet.

FIG. 11 illustrates a further alternative four-leaflet valve 110 of the present invention in plan view. As with the valve 100 of FIG. 10, the support structure 112 defines a somewhat rounded D-shaped orifice with two longer sides and two shorter sides. The four leaflets 114a, 114b, 114c, 114d are not all the same with the leaflet 114c on the bottom side being substantially larger than each of the other three. More particularly, the angular span of each of the leaflets is indicated between lines radiating outward from the effective center of the support structure 112, or flow axis. The three upper leaflets 114a, 114b, 114d each span the same angle $\alpha_1$, while the lower leaflet 114c spans an angle $\beta_1$, where $\beta_1 > \alpha_1$. In one embodiment, the angle $\beta_1$ is approximately 120°, while the angle $\alpha_1$ is approximately 80°. Again, the upper leaflet 114a substantially corresponds to the native anterior leaflet, while the remaining three leaflets 114b, 114c, 114d combine to simulate the native posterior leaflet.

FIG. 12 illustrates a still further alternative four-leaflet valve 120 of the present invention in plan view. As with the valve 100 of FIG. 10, the support structure 122 defines a somewhat rounded D-shaped orifice with two longer sides and two shorter sides. The four leaflets 124a, 124b, 124c, 124d are not all the same with the leaflet 124a on the top side being substantially larger than each of the other three. More particularly, the angular span of each of the leaflets is indicated between lines radiating outward from the effective center of the support structure 122, or flow axis. The three lower leaflets 124b, 124c, 124d each span the same angle $\alpha_2$, while the upper 124a spans an angle $\beta_2$, where $\beta_2 > \alpha_2$. In one embodiment, the angle $\beta_2$ is approximately 120°, while the angle $\alpha_2$ is approximately 80°. Like the other two valves 100, 110, the upper leaflet 124a substantially corresponds to the native anterior leaflet, while the remaining three leaflets 124b, 124c, 124d combine to simulate the native posterior leaflet.

It will also be appreciated by those of skill in the relevant art that various changes may be made to the examples and embodiments of the invention described in this provisional application, without departing from the intended scope of the invention. The particular embodiments of the invention described herein are thus to be understood as examples of the broader inventive concept disclosed in this application.

What is claimed is:

1. A prosthetic heart valve for implant at a valve annulus, comprising:

a non-planar support frame defining a non-circular orifice about an axis along an inflow-outflow direction, the orifice having a longer dimension along a major axis and a shorter dimension along a perpendicular minor axis, the support frame having an inflow edge and commissures extending generally axially therefrom in the outflow direction to an axial height of at least 6 mm; and four separate flexible leaflets arranged in two pairs of diametrically opposed, symmetric leaflets, wherein a first pair of leaflets is substantially smaller than a second pair of leaflets each being separately mounted for movement on the support frame and being supported between the axially extending commissures to provide a one-way valve in the non-circular orifice.

2. The prosthetic heart valve of claim 1, wherein the four separate flexible leaflets are arranged in a first pair and a second pair of leaflets, each pair being diametrically opposed across the orifice, and wherein each one of the first pair of leaflets is substantially smaller than either leaflet of the second pair.

3. The prosthetic heart valve of claim 1, further including a sewing ring attached to and projecting outward from the support frame adjacent the inflow edge.

4. The prosthetic heart valve of claim 1, wherein the leaflets of the second pair are differently sized from each other.

5. The prosthetic heart valve of claim 1, wherein the support frame comprises an undulating outflow edge including four alternating inflow cusps and flexible outflow commissures that extend generally axially in the outflow direction in a cantilevered fashion, and wherein each of the separate flexible leaflets has a cusp edge mounted to an inflow cusp of the support frame and two commissure edges mounted to adjacent outflow commissures of the support frame.

6. A prosthetic heart valve for implant at a valve annulus, comprising:
   a support frame defining a non-circular orifice about an axis along an inflow-outflow direction, the orifice having a longer dimension along a major axis and a shorter dimension along a perpendicular minor axis, the support frame having an undulating outflow edge including four alternating inflow cusps and flexible outflow commissures that extend generally axially in the outflow direction in a cantilevered fashion; and
   four separate flexible leaflets each seperately mounted for movement along the outflow edge of the support frame to provide a one-way valve in the orifice, each leaflet including a cusp edge mounted to an inflow cusp of the support frame and two commissure edges mounted to adjacent outflow commissured of the support frame,
wherein the four separate flexible leaflets are arranged in a first pair and a second pair of leaflets, each pair being diametrically opposed across the orifice, and wherein the leaflets of the second pair are differently sized from each other.

7. The prosthetic heart valve of claim 6, wherein the valve is symmetric about two axes.

8. The prosthetic heart valve of claim 6, wherein the support frame comprises an undulating wireform and a stent therearound, the wireform generally defining the outflow edge of the support frame and having inverted V-shaped commissures through which the commissure edges of two adjacent leaflets extend, the stent having commissure posts of approximately the same height as the wireform commissures and to which the extending commissure edges attach.

9. The prosthetic heart valve of claim 8, wherein the wireform and stent are made of synthetic materials and the leaflets are made of biological sheet material.

10. The prosthetic heart valve of claim 6, wherein the support frame commissures have an axial height of at least 6 mm.

11. A prosthetic heart valve for implant at a valve annulus, comprising:
   a non-planar support frame defining an elliptical orifice about an axis along an inflow-outflow direction and made of a material that mimics fibrous commissures of natural heart valves; and
   four separate flexible leaflets having cusps and commissures each separately mounted for movement on the support frame to form three-dimensional leaflets supported at their edges by the support frame and together provide a one-way valve in the orifice, wherein at least one of the leaflets is substantially smaller than at least one of the other leaflets.

12. The prosthetic heart valve of claim 11, wherein the four separate leaflets comprise a first pair and a second pair of leaflets, each pair being diametrically opposed across the orifice, and wherein each leaflet of the first pair is substantially smaller than either leaflet of the second pair.

13. The prosthetic heart valve of claim 12, wherein the two leaflets of the first pair are identically sized.

14. The prosthetic heart valve of claim 12, wherein the two leaflets of the second pair are identically sized.

15. The prosthetic heart valve of claim 11, wherein the support frame has an undulating outflow edge including four alternating inflow cusps and flexible outflow commissures that extend generally axially in the outflow direction in a cantilevered fashion and having an axial height of at least 6 mm.

16. The prosthetic heart valve of claim 11, wherein the support frame is made at least in part of metal.

17. The prosthetic heart valve of claim 11, wherein the support frame includes an undulating wireform defining alternating cusps and commissures.

18. The prosthetic heart valve of claim 17, wherein the support frame further includes a stent surrounding the wireform and having an outflow edge that mimics the undulating shape of the wireform.

19. The prosthetic heart valve of claim 1, wherein the ratio of the shorter dimension to the longer dimension is approximately 3:4.

* * * * *